US007741037B2

(12) United States Patent
Renthal

(10) Patent No.: US 7,741,037 B2
(45) Date of Patent: *Jun. 22, 2010

(54) METHOD FOR PHEROMONE DISCOVERY IN INSECTS

(75) Inventor: Robert David Renthal, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 668 days.

This patent is subject to a terminal disclaimer.

(21) Appl. No.: 11/355,444

(22) Filed: Feb. 16, 2006

(65) Prior Publication Data

US 2006/0127944 A1 Jun. 15, 2006

Related U.S. Application Data

(63) Continuation of application No. 10/426,918, filed on Apr. 30, 2003, now Pat. No. 7,074,572.

(60) Provisional application No. 60/376,451, filed on Apr. 30, 2002.

(51) Int. Cl.
| | |
|---|---|
| C12Q 1/68 | (2006.01) |
| G01N 33/53 | (2006.01) |
| A01N 25/00 | (2006.01) |
| C07K 14/00 | (2006.01) |
| C40B 40/00 | (2006.01) |
| C40B 40/10 | (2006.01) |
| C07H 21/02 | (2006.01) |

(52) U.S. Cl. ............................ 435/6; 435/7.1; 424/405; 530/350; 506/13; 506/14; 506/16; 506/18; 536/23.1; 536/24.33

(58) Field of Classification Search ....................... None
See application file for complete search history.

(56) References Cited

U.S. PATENT DOCUMENTS

| | | | | |
|---|---|---|---|---|
| 5,030,722 | A | 7/1991 | Snyder et al. | 536/27 |
| 5,068,453 | A | 11/1991 | Kuwahara et al. | 568/494 |
| 5,128,246 | A | 7/1992 | Snyder et al. | 435/69.1 |
| 5,260,270 | A | 11/1993 | Snyder et al. | 514/2 |
| 5,772,983 | A | 6/1998 | O'Connell et al. | 424/9.2 |
| 6,316,221 | B1 | 11/2001 | Leal et al. | 435/69.1 |
| 6,440,406 | B1 | 8/2002 | Lopez, Jr. et al. | 424/84 |
| 7,074,572 | B2 * | 7/2006 | Renthal | 435/7.1 |

OTHER PUBLICATIONS

Prestwich GD., Proteins that smell: Pheromone recognition and signal transduction. Bioorganic & Med. Chem., 1996, vol. 4 (3): 505-513.*
Zhu et al., Global analysis of protein activities using proteome chips. Scinece, 2001, vol. 293: 2101-2105.*
NPLEntrez (One page summary).*
NPLGoogle (Two page summary).*
NPLSCIRUS (Three page summary).*

Altner and Prillinger, "Ultrastructure of invertebrate chemo-, thermo-, and hygroreceptors and its functional significance," *Int. Rev. Cytol.*, 67:69-139, 1980.
Beuckmann et al., "Binding of biliverdin, bilirubin, and thyroid hormones to lipocalin-type prostaglandin D synthase," *Biochemistry*, 38:8006-8013, 1999.
Breer et al. "Rapid kinetics of second messenger formation in olfactory transduction," *Nature*, 344:65-68, 1990.
Briand et al., "Odorant and pheromone binding by aphrodisin, a hamster aphrodisiac protein," *FEBS Lett.*, 476:179-185, 2000.
Campanacci et al., "Recombinant pheromone binding protein 1 from *Mamestra brassicae* (MbraPBP1)," *Eur. J. Biochem.*, 264:707-716, 1999.
Caron et al., "Solubility and characterization of the β-adrenergic receptor binding sites of frog erythrocyte," *J. Biol. Chem.*, 251:2374-2384, 1976.
Catimel et al., "Micropreparative ligand fishing with a cuvette-based optical mirror resonance biosensor," *J. Chrom. A*, 869:261-273, 2000.
Danty et al., "Cloning and expression of a queen pheromone-binding protein in the honeybee: an olfactory-specific, developmentally regulated protein," *J. Neurosci.*, 19:7468-7475, 1999.
Davis and Han, "Neuroantomy: Mushrooming mushroom bodies," *Curr. Biol.*, 6:146-148, 1996.
Dickens et al., "Olfaction in a hemimetabolous insect: antennal-specific protein in adult *Lygus lineolaris* (Heteroptera: Miridae)," *J. Insect Physiol.*, 41:857-867, 1995.
Du and Prestwick, "Protein structure encodes the ligand binding specificity in pheromone binding proteins," *Biochemistry*, 34:8726-8732, 1995.
Du et al., "Odorant binding by a pheromone binding protein: active site mapping by photoafinity labeling," *Biochem.*, 33:4812-4819, 1994.
Flower, "The lipocalin protein family: structure and function," *Biochem. J.*, 318:1-14, 1996.
Glancey et al., "Field tests with synthetic components of the queen recognition pheromone of the red imported fire ant, *Solenopsis invicta*," *Sociobiology*, 9:19-30, 1984.
Gronenberg et al., "Age-dependent and task-related morphological changes in the brain and the mushroom bodies of the ant camponotus floridanus," *J. Exp.Biol.*, 199:2011-2019, 1996.
Grotewiel et al., "Integrin-mediated short-term memory in *Drosophila*," *Nature*, 391:455-460, 1998.
Hansson and Anton, "Function and morphology of the antennal lobe: new developments," *Annu. Rev. Entomol.*, 45:203-231, 2000.

(Continued)

*Primary Examiner*—Ganapathirama Raghu
(74) *Attorney, Agent, or Firm*—Fulbright & Jaworski LLP

(57) ABSTRACT

The present invention is directed generally to a method of identifying an insect pheromone. Initially, a candidate insect pheromone-binding protein is obtained and sequenced. Specific proteins may then be selected by observing the pattern of pheromone-binding protein expression in the insect stage, phase or caste; and/or in the antenna and other sensilla by, for example, in situ hybridization; and/or by comparison with sequence of known pheromone binding proteins. A composition of one or more pheromones may then be contacted with the pheromone-binding protein. Any pheromones bound to the protein may then be eluted and analyzed.

30 Claims, 2 Drawing Sheets

OTHER PUBLICATIONS

Hekmat-Scafe et al., "Coexpression of two odorant-binding protein homologs in *Drosophila*: implications for olfactory coding," *J. Neuroscience*, 17:1616-1624, 1997.

Hildebrand and Shepard, "Mechanisms of olfactory discrimination: converging evidence for common principles across phyla," *Annu. Rev. Neurosci.*, 20:595-631, 1997.

Holden et al., "The molecular structure of insecticyanin form the tobacco hormworm *Manduca sexta* L. at 2.6 Å resolution," *EMBO J.*, 6:1565-1570, 1987.

Hölldobler and Wilson, In: *The Ants*, pp. 263-269, 630-633, Belknap Press, Cambridge, MA, 1990.

Horst et al., "NMR structure reveals intramolecular regulation mechanism for pheromone binding and release," *Proc. Natl. Acad. Sci. USA*, 98:14374-14379, 2001.

Hovemann et al., "*Drosophila melanogaster* NADPH-cytochrome P450 oxidoreductase: pronounced expression in antennae may be related to odorant clearance," *Gene*, 189:213-219, 1997.

Ishida et al., "Protein that makes sense in the Argentine ant," *Naturwiss*, 89:505-507, 2002.

Isidoro et al., "Antennal glands in queen and worker of the fire ant, *Solenopsis invicta* buren: first report in female social Aculeata (Hymenoptera, Formicidae)," *Insectes Soc.*, 47:236-240, 2000.

Jouvenaz et al., "A survey for pathogens of fire ants, *Solenopsis* Spp, in the southeastern United States," *Florida Ent.*, 60:275-279, 1977.

Keller and Ross, "Selfish genes: a green beard in the red fire ant," *Nature*, 394:573-575, 1998.

Kern and Bestmann, "Antennal electrophysiological responsiveness of the ponerine ant leptogenys diminuta to trail and recruitment pheromones and its structure analogs," *Naturwissenschaften*, 80:424-427, 1993.

Kim et al., "LUSH odorant-binding protein mediates chemosensory responses to alcohols in *Drosphila melanogaster*," *Genetics*, 150:711-721, 1998.

Korchi et al., "cDNA cloning of an adult male putative lipocalin specific to tergal gland aphrodisiac secretion in an insect (*Leucophaea maderae*)," *FEBS Lett.*, 449:125-128, 1999.

Krieger and Breer, "Olfactory reception in invertebrates," *Science*, 286:720-723, 1999.

Krieger and Ross, "Identification of a major gene regulating complex social behavior," *Science*, 295:328-332, 2002.

Krieger et al., "Binding proteins from the antennae of *Bombyx mori*," *Insect Biochem. Biol.*, 26:297-307, 1996.

Krieger et al., "Identification of a cyclic nucleotide- and voltage-activated ion channel from insect antennae," *Insect Biochem. Molec. Biol.*, 29:255-267, 1999.

Lartigue et al., "X-ray structure and ligand binding study of a moth chemosensory protein," *J. Biol. Chem.*, 277:32094-32098, 2002.

Laurent and Davidowitz, "Encoding of olfactory information with oscillating neural assemblies," *Science*, 265:1872-1875, 1994.

Leal et al., "Disulfide structure of the pheromone binding protein from the silkworm moth, *Bombyx mori*," *FEBS Lett.*, 464:85-90, 1999.

Liu et al., "Gene characterized for membrane desaturase that produces (E)-11 isomers of mono- and diunsaturated fatty acids," *Proc. Natl. Acad. Sci. USA*, 99(2):620-624, 2002.

MacLeod et al., "Who reads temporal information contained across synchronized and oscillatory spike trains?" *Nature*, 395:693-698, 1998.

Mameli et al., "Soluble proteins in chemosensory organs of phasmids," *Insect Biochem. Molec. Biol.*, 26:875-882, 1996.

Meillour et al., "Purification and characterization of multiple forms of odorant/pheromone binding proteins in the antennae of *Mamestra brassicae* (Noctuidae)," *Insect Biochem. Molec. Biol.*, 26:59-67, 1996.

Merivee et al., "Distribution of olfactory and some other antenna sensilla in the male click beetle *Agriotes obscurus* L. (Coleoptera: elateridae)," *Int. J. Insect Morphol. & Embryol.*, 26:75-83, 1997.

Mori et al., "Colony founding in Polyergus rufescens: the role of the Dufour's gland," *Insectes Sociaux*, 47:7-10, 2000.

Narayanaswami and Ryan, "Molecular basis of exchangeable apolipoprotein function," *Biochim. Biophys. Acta*, 1483:15-36, 2000.

Navasero and Elzen, "Sensilla on the antennae, foretarsi and palpi of microplitis croceipes (cresson)(hymenoptera:braconidae)," *Proc. Ent. Soc. Wash.*, 93:737-747, 1991.

Paesen, and Happ, "The B proteins secreted by the tubular accessory sex glands of the male mealworm beetle, Tenebrio molitor, have sequence similarities to moth pheromone-binding proteins," *Insect Biochem. Molec. Biol.*, 25:401-408, 1995.

Pelosi and Maida, "Odorant-binding proteins in insects," *Comp. Biochem. Physiol.*, 111B:503-514, 1995.

Picimbon and Leal, "Olfactory soluble proteins of cockroaches," *Insect Biochem. Molec. Biol.*, 29:973-978, 1999.

Pikielny et al., "Members of a family of drosophila putative ordorant-binding proteins are expressed in different subsets of olfactory hairs," *Neuron.*, 12:35-49, 1994.

Pilpel and Lancet, "Good reception in fruitfly antennae," *Nature*, 398:285,287, 1999.

Prestwich, "Bacterial expression and photoaffinity labeling of a pheromone binding protein," *Protein Science*, 2:420-428, 1993.

Raming et al., "Molecular cloning of pheromone binding proteins in insect antennae," *Biol. Chem.*, 371:1028-1029, 1990.

Renthal et al., "Sensory reception in fire ants," *Texas Imported Fire Ant Research Project, Final Report*, Oct. 2001, pp. 1-3, http://fireant.tamu.edu/research/ProgressReports/01_03/oct01/Renthal.pdf.

Renucci et al., "Phosphorylation of cockroach antennal polypeptides: effects of second messengers and pheromonal blend," *Experientia*, 52;762-768, 1996.

Rothemund et al., "A new class of hexahelical insect proteins revealed as putative carriers of small hydrophobic ligands," *Structure*, 7:1325-1332, 1999.

Rubin et al., "Comparative genomics of eukaryotes," *Science*, 287:2204-2215, 2000.

Sandler et al., "Sexual attraction in the silkworm moth: structure of the pheromone-binding-bombykol complex," *Chemistry and Biology*, 7:143-151, 2000.

Skoulakis et al., "Preferential expression in mushroom bodies of the catalytic subunit of protein kinase A and its role in learning and memory," *Neuron.*, 11:197-208, 1993.

Smith et al. "Exchangeable apolipoproteins of insects share a common structural motif," *J. Lipid Res.*, 35:1976-1984, 1994.

Steinbrecht and Stankiewicz, "Molecular composition of the all of insect olfactory sensilla—the chitin question," *J. Insect Physiol.*, 45:785-790, 1999.

Tsuchihara et al., "A putative binding protein for lipophilic substances related to butterfly oviposition," *FEBS Lett.*, 478:299-303, 2000.

Tuccini et al., "Putative odorant-binding protein in antennae and legs of *Carausius morosus* (Insecta, Phasmatodea)," *Insect. Biochem. Molec. Biol.*, 26:19-24, 1996.

Vander Meer et al., "Isolation of the trail recruitment pheromone of *Solenopsis invicta*," *J. Chem. Ecology*, 14:825-838, 1988.

Vincent et al., "Complexes of porcine odorant binding protein with odorant molecules belonging to different chemical classes," *J. Mol. Biol.*, 300:127-139, 2000.

Vogt et al., "Odorant-binding-protein subfamilies associated with distinct classes of olfactory receptor neurons in insects," *J. Neurobiology*, 22:74-84, 1991.

Vosshall et al., "A spatial map of olfactory receptor expression in the drosophila antenna," *Cell*, 96:725-736, 1999.

Weinzierl et al., "Insect attractants and traps," *Alternatives in Insect Management by the Office of Entomology*, University of Illinois at Urbana-Champaign, Jun. 1995, revised Jun. 2005, EDIS website at http://edis.ifas.ufl.edu.

Willett and Harrison, "Pheromone binding proteins in the European and Asian corn boreres: no protein change associated with pheromone differences," *Insect Biochem. and Mol. Biol.*, 29:277-284, 1999.

Wojtasek and Leal, "Conformational change in the pheromone-binding protein from *Bombyx mori* induced by pH and interaction with membranes," *J. Biol. Chem.*, 274:30950-30956, 1999.

Wojtasek et al., "Attracted or repelled?—a matter of two neurons, one pheromone binding protein, and a chiral center," *Biochem. Biophys. Res. Commun.*, 250:217-222, 1998.

Wojtasek et al., "Identification and cloning of odoarant binding proteins from the Scarab beetle Phyllopertha diversa," *Biochem. Biophys. Res. Commun.*, 263:832-837, 1999.

Zacharuk, "Antennae and sensilla," *Comprehensive Insect Physiol., Biochem. and Pharm.*, 6:1-69, 1985.

* cited by examiner

METHOD FOR PHEROMONE DISCOVERY IN INSECTS

The application is a continuation of co-pending application Ser. No. 10/426,918 filed Apr. 30, 2003, now issued as U.S. Pat. No. 7,074,572, which claims priority to co-pending U.S. Provisional Patent Application Ser. No. 60/376,451, filed on Apr. 30, 2002. The entire text of each of the above-referenced disclosures is specifically incorporated herein by reference.

BACKGROUND OF THE INVENTION

I. Field of Invention

The present invention relates generally to a method for isolating insect pheromones. More particularly, the present invention relates to a method for purifying pheromone-binding proteins, and then using the purified proteins to capture insect pheromones.

II. Description of Related Art

Insects receive information from external chemical signals by means of receptors located primarily in the antenna. The dendrites of olfactory receptor neurons in the antenna typically are located in sensilla, thin hair-like structures which protrude from the antennal surface (Altner and Prillinger, 1980; Zacharuk, 1985). Receptor neurons appear to be specialized for particular substances, and each olfactory sensilla may contain dendrites from many different receptor neurons. The plasma membranes of the dendrites contain the olfactory receptor proteins (Hildebrand and Shepard, 1997; Krieger and Breer, 1999).

When activated by an odor or pheromone molecule, the receptors couple to G proteins, which in turn alter ion channel conductance in the receptor neuron membrane, mostly via an $IP_3$ pathway (Breer et al., 1990), although a parallel cAMP pathway may also occur (Krieger et al., 1999). The receptor neurons form synapses with interneurons in the glomeruli of the antennal lobe of the brain (Hansson and Anton, 2000). Projection neurons carry the signals from the antennal lobe to the mushroom body, where synchronous firing is observed after odor detection (Laurent and Davidowitz, 1994). Olfactory information appears to be encoded in the synchronization. Neurons involved in decoding have been identified outside the mushroom body, forming synapses with the intrinsic neurons of the β lobe (McLeod et al., 1998). cAMP signaling pathways in the mushroom body are used for storage of olfactory memory (Skoulakis et al., 1993; Davis and Han, 1996), and short-term memory formation involves α-integrin (Grotewiel et al., 1998).

Pheromones are a major communication channel for insects. For instance, ants use pheromones to identify the colony, signal alarms, mark trails to food, attract workers to brood and to the queen, and bring males and females together for mating (Hölldobler and Wilson, 1990). Queen pheromones also may be involved in the maintenance of polygyny (multiple queen colonies) (Keller and Ross, 1998; Ross and Keller, 1998; Krieger and Ross, 2002) and in founding slave-making colonies (Mori et al., 2000). In addition, foraging, feeding, and defending the nest depend on detection of general odors and tastes and on detection of kairomones (signals from other species). Similarly, many other insects rely upon pheromones, often for similar types of communications.

The isolation and identification of various pheromones from insects is significant for a variety of reasons. For instance, these pheromones would assist in uncovering new basic information about the olfactory communication system and social behavior of social insects. Furthermore, knowledge of the pheromones would have direct application to management and control of various insect pests, including termites and fire ants. Unfortunately, pheromones are present in small quantities in natural sources, and may be difficult to isolate using conventional techniques. A need therefore exists for new methods of isolating pheromones.

SUMMARY OF THE INVENTION

The present invention relates generally to new methods of identifying, isolating, and/or using insect pheromones.

In some embodiments, the invention relates to methods of identifying an insect pheromone comprising: obtaining one or more candidate insect pheromone-binding protein; contacting the candidate pheromone-binding protein with a composition comprising one or more insect pheromones under conditions conducive to allow at least one suitable pheromone, if present, to bind to the candidate pheromone binding protein; eluting any pheromone bound to the isolated candidate pheromone binding protein. These methods may further comprise isolating or purifying the eluted pheromone, using any method known to one of skill in the art. Additionally, the method may further comprise using the isolated pheromone to attract an insect to poison; to repel an insect from an area intended to be kept pest-free; or to interfere with insect behavior, such as mating or foraging, resulting in the extermination of the insect. The present invention is equally applicable to insects in general including, but not limited to, a member of the genus *Anopheles*, a member of the genus *Solenopsis*, a member of the genus *Aphids*, and scale insects, and any other insects that are human, animal and/or plant pests.

In certain exemplary, but not limiting, embodiments, the pheromone-binding protein is from an ant. In more specific non-limiting examples, the ant is a red imported fire ant (*Solenopsis invicta*). In some cases, the ant is a male ant, worker ant, monogyne queen ant, or polygyne queen ant.

In some cases, the candidate pheromone binding protein is obtained by a process comprising two-dimensional polyarcylamide gel electrophoresis or chromatography.

In some embodiments, obtaining the candidate pheromone binding protein further comprises: obtaining a first sequence analysis of the candidate pheromone-binding protein; and selecting one or more pheromone-binding proteins of interest from the sequenced pheromone-binding proteins. In some cases, the first sequence analysis is performed by mass spectrometry or Edman degradation. The sequence analysis can be either a full or partial sequence analysis. Selecting the pheromone-binding protein of interest, in some non-limiting embodiments, comprises: comparing the first sequence analysis with a second sequence of a known insect pheromone- or odorant-binding protein; and choosing one or more of the sequenced pheromone-binding proteins that have a sequence similar to the second sequence of the known insect pheromone- or odorant-binding protein.

In some preferred embodiments, the candidate pheromone-binding protein is a recombinant pheromone-binding protein. For example, the recombinant pheromone-binding protein may be obtained by a method comprising amplifying a nucleic acid sequence encoding a polypeptide comprising the candidate pheromone-binding protein. Such a method may comprise: obtaining a PCR primer constructed using the candidate pheromone-binding protein; using the PCR primers to amplify a nucleic acid sequence from cDNA produced from mRNA obtained from the insect sample; and expressing the nucleic acid sequence in an expression system to produce the candidate pheromone-binding protein. In some embodiments, the DNA library comprises all or part of an *S. invicta* genome, an *Anopheles* genome, an *Aphids* genome, a scale insect genome, or any other insect genome. The candidate insect pheromones of the composition are extracted, for example, from whole insects, parts of insects, larvae, pupae, or nest middens. Typically, the pheromones are extracted with a solvent, for example, a solvent comprising pentane, hexane, methylene chloride, chloroform, methanol, diethyl ether, or a combination thereof. Further, the composition can be a vapor.

In some specific embodiments, the invention relates to methods of identifying an insect pheromone comprising: obtaining one or more candidate pheromone-binding proteins; performing a sequence analysis of the candidate pheromone-binding proteins; determining a nucleic acid sequence that encodes the candidate pheromone-binding protein; recombinantly expressing the candidate pheromone-binding protein from the nucleic acid sequence; contacting the candidate recombinant pheromone-binding protein with a second composition comprising one or more insect pheromones under conditions conducive to allow at least one suitable pheromone, if present, to bind to the recombinant pheromone-binding protein; and eluting any pheromone that is bound to the recombinant pheromone- or odorant-binding protein. These methods may further comprise isolating or purifying the eluted pheromone. Additionally, the sequence analysis may be either a partial or complete sequence analysis.

In some embodiments of the invention, the candidate recombinant pheromone-binding protein is placed on a solid support prior to the elution step. The solid support may comprise, for example, agarose, plastic, or glass. In some cases, the second composition is a vapor or solvent extract. The method may further comprise using the candidate pheromone-binding protein to construct a primer, and using the primer to identify a genomic sequence from an existing DNA library.

In other embodiments, the invention relates to one or more insect pheromones isolated by the above-discussed methods.

In further embodiments, the invention relates to methods for assaying the specific binding of a pheromone to a pheromone-binding protein, wherein the pheromone is isolated by a process comprising: obtaining one or more candidate insect pheromone-binding proteins; contacting the candidate pheromone-binding protein with a composition comprising one or more insect pheromones under conditions conducive to allow at least one suitable pheromone, if present, to bind to the candidate pheromone-binding protein; eluting the pheromone that is bound to the isolated pheromone-binding proteins; and collecting the eluted pheromone. In specific embodiments, the assay comprises: contacting a sample comprising a pheromone-binding protein with the eluted pheromone under conditions conducive to allow at least one of the eluted pheromone to bind to the pheromone-binding protein of the sample; and measuring the specific binding of the eluted pheromone to the pheromone-binding protein of the sample. For example, the specific binding of the eluted pheromone may be measured by a resonant mirror detector, a plasmon resonance detector, affinity chromatography, a vapor equilibration method, a precipitation method, or a radioligand exchange method.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

I. The Present Invention

Figure 1:
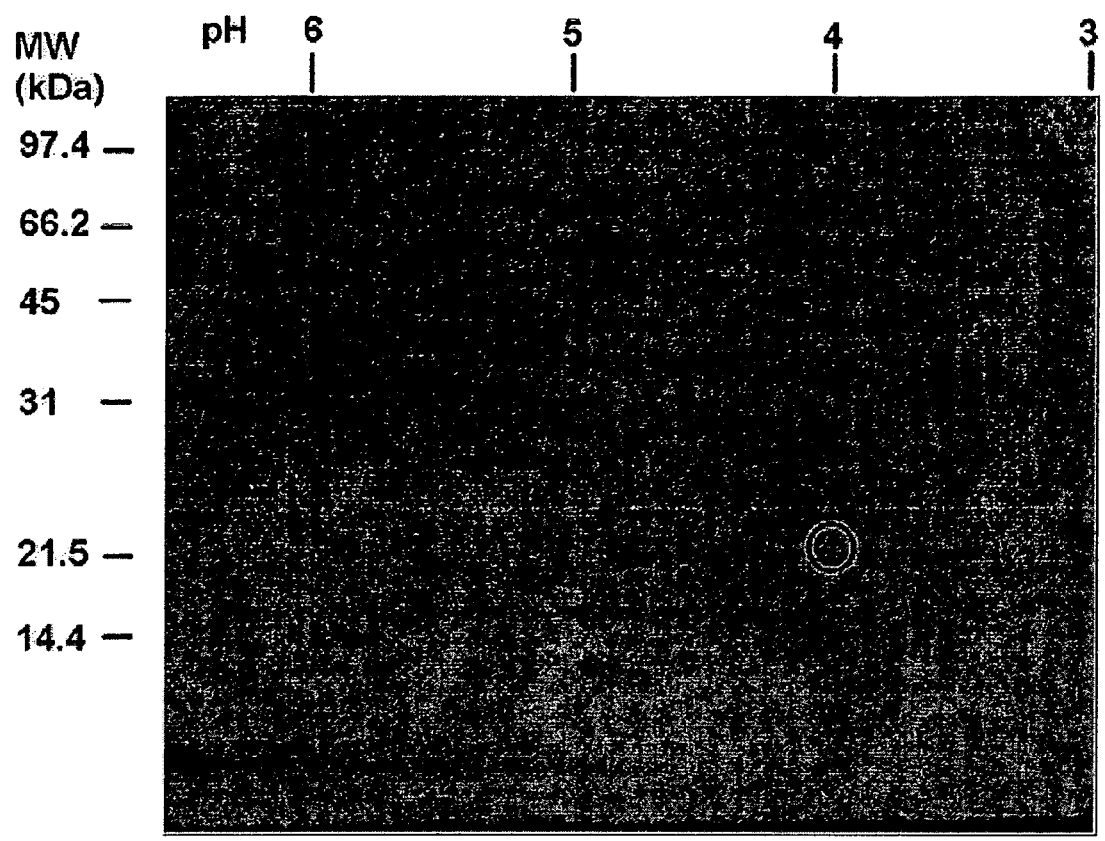
FIG. 1. Electroblot of two-dimensional polyacrylamide gel electrophoresis of proteins extracted from male fire ant antennae. Horizontal dimension: isoelectric focusing, from pI=6.5 (left) to pI=3.0 (right). Vertical dimension, SDS-PAGE, with molecular weight markers indicated on the left (from bottom: 14.4, 21.5, 31, 45, 66.2, and 97.4 kDa). Blot stained with Coomassie blue and imaged with a CCD camera. Circled spot corresponds to apolipophorin-III.

The present invention is directed generally to a method of identifying an insect pheromone. Initially, a candidate insect pheromone- or odorant-binding protein is obtained. In the present invention, the general terms "odorant-binding protein" and "pheromone-binding protein" are used to refer to insect proteins that are known as odorant-binding proteins (OBP), pheromone binding protein (PBP), chemosensory protein (CSP), sensory appendage protein (SAP), and also other hydrophobic ligand-binding proteins which may be found in insect antennae or other insect chemosensory organs and which have a biological function to bind to insect pheromones or metabolic precursors or products of insect pheromones. The protein may be obtained in a variety of ways. For instance, the genomic sequences of odorant and pheromone binding proteins obtained from the antennae of an insect may initially be determined. A selected protein may then be used to identify pheromones. For instance, the selected protein may be exposed to a solution comprising multiple pheromones. Any pheromone that is bound to the selected protein may then be eluted and analyzed.

II. OBPs and PBPs

Olfactory sensilla have thin chitin-based cuticle (Steinbrecht and Stankiewicz, 1999) containing small pores through which odors and pheromones may pass. The extracellular fluid inside the sensilla, the antennal lymph, contains high concentrations of odorant-binding proteins (OBPs) or pheromone-binding proteins (PBPs), which capture the odorants or pheromones, respectively (Pelosi and Maida, 1995). Since volatile odorants or pheromones typically are not very soluble in water, the OBPs or PBPs capture and concentrate these molecules. At least one OBP has been shown to be essential for detection of a specific odor (Kim et al., 1998). OBP/PBPs may also be involved in interaction with the olfactory receptors and in removal of odorants from the antennal lymph. Often more than one OBP and PBP occurs in a particular insect species.

The different OBPs or PBPs are localized to particular subgroups of sensilla (Vogt et al., 1991; Pikelny et al., 1994). Some sensilla may contain more than one type of OBP (Hekmat-Scafe et al., 1997). Thus, their localization resembles the distribution of olfactory receptor neurons, which appear to specialize in particular odors, but which may occur together with different types of receptor neurons in the same sensillum. However, the OBPs and PBPs are not as specific in their binding characteristics as the membrane-bound olfactory receptors. For example, two different species of moth, which use two different isomers of the same molecule for the sex pheromone, have the same PBP for both molecules (Willett and Harrison, 1999). Furthermore, a PBP was found to be incapable of distinguishing between the R and S enantiomers of a beetle pheromone, in contrast to the olfactory receptors for this pheromone, which are enantiomer-specific (Wojtasek et al., 1998). The dissociation constants for ligands from PBPs are in the micromolar range (Du and Prestwich, 1995), which is several orders of magnitude weaker than ligand dissociation constants found for G-coupled receptors (Caron and Lefkowitz, 1976), but similar to the interactions found for vertebrate OBPs (Vincent et al., 2000). Ligand release appears to be triggered by low pH, which causes a substantial conformational change in the OBP (Wojtasek and Leal, 1999; Horst et al., 2001). The negative surface charge of the receptor membrane may be sufficient to lower the surface pH to the level which triggers the ligand-releasing conformational change.

Although the insect olfactory system resembles the vertebrate system in broad outline, many details are quite different. For example, the major insect OBPs and PBPs are from a different protein family than the vertebrate OBPs and PBPs. Vertebrate OBPs are lipocalins, a family of hydrophobic ligand binding proteins that includes serum retinol binding protein and orosomucoid (Flower, 1996). Lipocalins have been found in insects but so far not in the antenna (Holden et al., 1987; Korchi et al., 1999; Tsuchihara et al., 2000). The structural differences between lipocalins and insect OBP/PBPs have been proven by X-ray diffraction and NMR (Sandler et al., 2000; Horst et al., 2001). In contrast to the β-barrel structure of lipocalins, the insect PBP folds into a basket of six α-helices surrounding a hydrophobic pocket where the pheromone molecule binds. The insect OBP/PBP sequences all have six conserved cysteines in disulfide bonds (Leal et al., 1999). Proteins related to the insect OBP/PBP family include the B-protein of the tubular accessory gland secretion of *Tenebrio molitor* (Paesen and Happ, 1995), and also *Tenebrio* hemolymph protein THP12 (Rothemund et. al., 1999). Although most of the OBP/PBPs involved in insect olfaction appear to belong to this hexahelical protein family, several putative OBPs have been reported with different structures (Mameli et al., 1996; Picimbon and Leal, 1999; Ishida et al., 2002). This alternative odorant- and pheromone-binding protein family is referred to as the chemosensory protein (CSP) or sensory appendage protein (SAP) family.

In *Drosophila menalogaster*, about 50 different olfactory receptor genes and 14 different OBP/PBP genes have been identified in the complete genome (Rubin et al., 2000). It seems unlikely that many others will be discovered. Thus, the number of different olfactory receptor genes in *Drosophila* is quite small—a surprising result, considering that the much simpler organism *C. elegans* has about 1000 different olfactory receptor genes (Rubin et al., 2000). Although there is some speculation that this difference may have to do with an evolutionary advance in signal processing in insects (Pilpel and Lancet, 1999), there could be other explanations. For example, *Drosophila* may be a specialist in a narrow range of odors, requiring a highly focused olfactory system. Evidence for this comes from studies of the glomeruli. *Drosophila* has only about 50 glomeruli in each antennal lobe. By contrast, the carpenter ant *Camponotus floridanus* has around 200 (Gronenberg et al., 1996). Presumably the demands of sociality would require a complex pheromone repertoire and therefore a larger signal processing apparatus. The *Drosophila* genome also has at least four CSP/SAPs. A second insect genome (*Anopheles gambiae*) was recently completed. *Anopheles* has at least 18 OBP/PBPs and 6 CSP/SAPs. No members of the apolipophorin-III (ALP-III) family could be identified in the *Drosophila* genome.

III. Identification of Pheromones

In one preferred embodiment of the present invention, pheromone-binding proteins and odorant-binding proteins from an insect are initially characterized. Much of the discussion herein focuses on the use of ants as the selected insect. However, one skilled in the art will recognize that the present invention is equally applicable to insects in general including, but not limited to, *Anopheles, Aphids,* scale insects, and any other insects that are human, animal and/or plant pests.

Pheromone-binding proteins and odorant-binding proteins may be obtained from parts, such as the antennae, of the selected insect. Polyacrylamide gel electrophoresis may be used to purify PBPs and OBPs from pooled antennal segments or other insect parts. Gel bands may be excised, followed by trypsin digestion and mass spectrometric sequence analysis. Alternatively, gels may be electroblotted to medium such as PVDF membrane, and the N-terminal sequence may be determined by automated Edman degradation. The protein sequences may be used to design PCR primers to identify the nucleotide sequences, as well as related sequences, from purified antennal RNA, existing cDNA libraries or BAC libraries of the genome of the selected insect species, such as the *S. invicta* genome. The sequences may be incorporated into an expression system to produce large quantities of protein. These proteins may then be used to search for and extract scarce ligands. Newly identified candidate pheromones may be tested by electrophysiology and bioassay.

In some embodiments of the invention an amino acid sequence, such as a partial amino acid sequence, may be obtained from a nucleotide sequence using standard molecular biology techniques and the codon table. Additionally, it is possible for one of ordinary skill in the art to use the codon table, and standard molecular biology techniques to obtain a nucleic acid sequence encoding all or part of a known amino acid sequence. For example, as discussed below, SEQ ID NO:1 is a nucleic acid sequence encoding all but the first three amino acids of SEQ ID NO:2. By using standard techniques one may obtain a nucleic acid encoding the entire amino acid sequence of SEQ ID NO:2. For example, one could create a synthetic nucleic acid encoding the first three amino acids and ligate that synthetic nucleic acid onto the native nucleic acid having the sequence of SEQ ID NO:1. Alternatively, one could use all or part of a nucleic acid having the sequence of SEQ ID NO:1 as a probe or primer to PCR a full length native nucleic acid segment encoding the entire amino acid segment of SEQ ID NO:2. Of course, this is only one example of the use of such techniques in the context of the invention. Standard molecular biology techniques are well known to those of skill in the art (see, Sambrook et al., 2000, Maniatis et al., 1990 and Ausbubel et al., 1994, incorporated herein by reference). Table I below list the codons for various species as are well known in the art.

TABLE 1

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

A. Determination of Partial Amino Acid Sequences of PBP/OBP

Insects that may be used in the present invention may be readily collected and stored using conventional techniques. For instance, if fire ants are used, the ants may be collected by the floatation method (Jouvenaz et al., 1977) and maintained in plastic trays (Hölldobler and Wilson, 1990). The antennae from the insects may then be collected, and placed in a suitable buffer solution to dissolve at least some of the PBPs and OBPs present in the antennae. The proteins may then be separated out of the solution using conventional techniques.

In one particular embodiment, antennae or other parts from the collected insects may be dissected on a freeze tray and, if necessary, subdivided into individual antennomers. Under a dissecting microscope, pooled antennomers may be transferred to a ceramic mortar in Laemmli (1970) SDS sample dilution buffer, or an immobilized pH gradient buffer containing 8 M urea, or other suitable buffer solution. For instance, 100-300 antennae may be transferred to a small ceramic mortar, such as one having a diameter of about 3 cm, in 20 µL of sample buffer. The antennae may then be ground with a pestle to break the cuticle. The extract and fragments may be washed into a centrifuge tube with additional aliquots of the sample buffer. For instance, the 20 µL of buffer solution containing the antennae may be washed into a 1.5 mL plastic centrifuge tube with two additional 20 µL aliquots of sample buffer. After centrifugation, the proteins may be separated by a variety of conventional techniques. For instance, the supernatant may be applied to a 15% polyacrylamide gel and the proteins separated by electrophoresis, or applied to an immobilized pH gradient strip and the proteins separated by isoelectric focusing followed by SDS-PAGE.

N-terminal sequences may be determined by electroblotting gels onto PVDF film (Matsudaira, 1987) followed by gas-phase Edman sequencing. Internal sequences may be obtained as follows. After staining, bands within a specified range, such as 14-23 kDa, may be excised and digested with trypsin, as described by Shevchenko et al. (1996) or other suitable compounds. The tryptic fragments may then be analyzed, such as in a Finnigan LCQ mass spectrometer, using the MS/MS capabilities of this Finnigan instrument to provide sequence information. Sequences obtained may be used to construct PCR primers.

B. Determination of Full Genomic Sequences of PBP/OBPs and Related Insect Proteins Antennae or other insect parts may be obtained by dissection of late stage pupae or adult insects that may be frozen on dry ice. mRNA may be isolated by homogenizing tissue in a suitable solution and then extracting and purifying it. For instance, mRNA may be isolated by homogenizing tissue in TNE:phenol (1:1), extracting proteins with phenol:chloroform 1:1 and purification with an oligo-dT column. A first strand cDNA may then be prepared. The strand may be prepared, for example, using MLV reverse transcriptase and either poly T or random octamer primers. The single strand cDNA may be used in PCR reactions with degenerate primers selected from the tryptic peptide sequences to obtain probes. Since OBP/PBPs are small (14-18 kDa), the coding domain of the cDNA should not be difficult to obtain by these methods of PCR amplification. Amplified PCR products may be ligated into the pGEM TA vector (Promega) and their sequences may be determined to ensure that they encode putative OBP/PBPs. Sequences may be compared with insect OBP/PBP sequences obtained from GenBank, EMBL and other sequence databases using suitable programs, such as Geneworks and BLAST. Isolates may be used to probe genomic libraries at lower stringency to search for additional PBP/OBP genes.

C. Distinguishing PBPs from GOBPs and Related Proteins

In cases where many OBP/PBP candidate sequences are obtained (e.g. from a complete genome), relevant PBP sequences may be distinguished from GOBP sequences by several methods.

1) A PBP involved in a specific behavior will typically be expressed only in those insects displaying the behavior. For example, a PBP that binds to a sex pheromone usually would be expressed exclusively in males or females. Therefore, the protein and the mRNA for it would be found only in males or only in females. This can be determined by gel electrophoresis or Northern blots. Similarly, in social insects, a PBP involved in a caste-specific behavior would be expressed only in a particular caste (e.g. nurses, soldiers or foragers).

2) The anatomical location of OBP/PBP expression in the insect may give clues about function. Some OBP/PBP-like proteins have been found in hemolymph or in secretions, and these proteins may be unrelated to pheromone binding (e.g. the B-proteins and the THP12 protein of *Tenebrio molitor*).

Such OBP/PBP-like proteins can be distinguished from PBPs by their location of expression. In situ hybridization may be used to locate the tissue where a candidate sequence is expressed. PBPs are expected to be primarily expressed in the antenna (although interesting exceptions may be found: for example, Gp-9 in *S. invicta* is expressed in the thorax).

3) There appear to be some sequence differences between PBPs and OBPs. More than 100 insect PBP/OBP sequences are identified in the Pfam database. Within this set, about 20 different sequences have been identified as PBPs and about 20 as GOBPs. All of the proteins in the insect OBP/PBP family have the distinctive sequence pattern CXXXC. In the PBPs, CXXXC is most often followed by L, whereas in the OBPs, it is most often followed by M, or an amino acid other than L. Furthermore, the C-terminal sequence after the sixth cysteine is, on average, 22 amino acids in PBPs and only 18 amino acids in GOBPs. Therefore, in attempting to distinguish a PBP sequence from a GOBP sequence, one should choose sequences containing CXXXCL and a C-terminal sequence of approximately 22 amino acids.

D. Expression of PBPs in a Recombinant System

Isolated PBP genes may be inserted into a pET22b plasmid, which permits high yield periplasmic expression of insect pheromone binding proteins in *E. coli* (Wojtasek and Leal, 1999). With this system, 6-10 mg pure *B. mori* PBP was produced per liter of culture. Recombinant PBP may be purified by the methods used by Wojtasek and Leal (1999) for *B. mori* PBP: successive chromatography on DEAE and hydroxyapatite, followed by gel permeation chromatography.

E. Identifying Pheromones

Expression of recombinant PBPs provides the means to identify the pheromones that bind to the proteins. This reverse strategy is known as "ligand fishing" (Catimel et al., 2000). In a typical experiment, a purified PBP is covalently attached to CNBr activated agarose. Extracts may be prepared from whole insects. For instance, with respect to ants, extracts may be prepared from whole ants (different castes, workers with different task assignments), ant cuticle, larvae, pupae, nest middens, dissected segments, and dissected glands. A variety of solvents may be tested for extraction, including, for example pentane, hexane, methylene chloride, chloroform, chloroform/methanol 1:1, and diethyl ether. Those skilled in the art will recognize that a variety of other extracts may also be used.

The extracts may be diluted into aqueous mixtures of solvents expected to be compatible with the native protein structure, such as, for example, dioxane, dimethyl formamide and DMSO. For example, dioxane may be tried initially because the *B. mori* PBP was crystallized in its native structure from a 50% solution of PEG 20,000 (Sandler et al., 2000), a polyether chemically similar to dioxane. It is preferable to seek a trade-off between high dilution of the extract and relatively low amount of organic solvent, for example about 10-25%, which will combine to keep the pheromones in solution and the protein in its native conformation. Ligands may be eluted from the PBP-agarose matrix by a combined pH-jump to, for example, pH 4.5 and an increase in the organic solvent content. Eluted material may be analyzed by a variety of means, including GC/MS.

Recombinant protein may be covalently attached to a suitable substrate, such as the aminosilane substrate of the Iasys biosensor cuvet (Affinity Sensors, Franklin, Mass.). After exposure to the previously described insect extracts, crude chromatographic fractions, or chromatographically purified components of extracts, specific binding to the PBP may be measured. Specific binding may be measured, for example, by the resonant mirror detector, following procedures similar to Beuckmann et al. (1999). This method may be used both for searching crude extracts for unknown pheromones and other ligands and for measuring equilibrium binding constants of purified candidate pheromones.

If affinity chromatography and the resonant mirror biosensor methods are inconclusive, other techniques may also be tried. One such technique is the vapor equilibration method. Samples of recombinant PBPs may be equilibrated with test vapors of crude pheromone extracts or purified fractions, according to the method used by Briand et al. (2000) to study ligand binding to hamster PBP. Bound ligand may extracted in pentane, methylene chloride, chloroform or other suitable organic solvent, and identified by GC/MS or other means.

Another technique that may be used is the precipitation method. This method, developed by Danty et al. (1999) for studying pheromone binding to *Apis* PBP, is similar to the vapor equilibration method except that the candidate pheromones are equilibrated with the PBP in the liquid phase and the protein-ligand complexes are precipitated with ammonium sulfate.

A third group of techniques that may be used is radioligand exchange methods. A competitive inhibitor binding assay may be possible if a non-native ligand can be identified which specifically binds to the PBP. The key feature of this inhibitor will be commercial availability with a radionuclide, or ease of incorporating a radionuclide. The inhibitor may be bound to the PBP and then dissociated by varying concentrations of non-labeled candidate pheromone. In an adaptation of the method of Du and Prestwich (1995) to study ligand binding, the pheromone-ligand complex may be removed from solution by binding to a coated plastic surface. The free ligand may be measured by determining the radioactivity remaining in the solution. Alternatively, in an adaptation of the method of Vincent et al. (2000), the displacement of radiolabeled pheromone from the PBP may be measured by vapor diffusion.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2A:
FIGS. 2A-2B. Illustrates silver staining of worker (FIG. 2A) and male (FIG. 2B) fire ant antennae, showing the sexual dimorphism in sensilla diversity. The stain identifies porous sensilla, which have an olfactory function. b=*sensilla basiconica*; t=*sensilla tricodea*. Light micrographs; scale bar=20 µm.
Figure 2B:
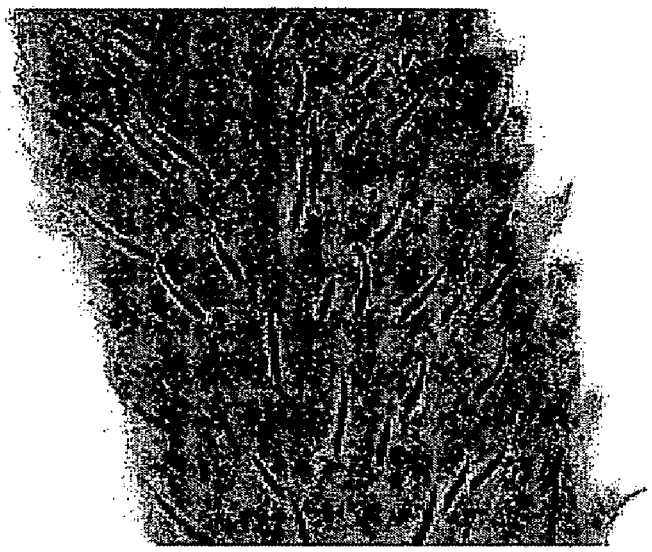

Inference of the Presence of a Simple Insect Pheromone System by Anatomical and Behavioral Analysis This example shows how observation of sexual dimorphism can reveal a simple pheromone system. Observation of whole red imported fire ants by light microscopy (100×) shows differences between male and female antennae. The female antenna has 10 (worker) or 11 (queen) segments, with the distal segments enlarged into a club. The male antenna lacks a club and contains 12 segments. The inventors examined the antennae by scanning electron microscopy. Ants were collected by shoveling the mound into a talc-lined bucket and slowly floating the ants to the surface with water (Jouvanaz et al., 1977). Males were identified by their black cuticle, small head and jaws, and filaform antennae. Ants were fixed overnight in 0.2 M phosphate buffer, pH 7.2 containing 2% glutaraldehyde and 2% paraformaledhyde, and then dehydrated in an alcohol series. Subsequently, the ants were critical point dried, coated with gold, and imaged in a JEOL 840 instrument. Female antennae showed a variety of external sensilla types on the club, including *sensilla basiconica* and four different types of *sensilla tricodea*. By contrast, the external sensilla on the male antennae were almost exclusively a single type of *sensilla tricodea* (FIG. 2). In separate preparations, the antennae were stained with silver to discover which sensilla contained pores (Navasero and Elzen, 1991). Ants were soaked for 5 min in 0.1 M $AgNO_3$. A few drops of Kodak Photoflo, or 10% Triton X-100 were added to keep the ants submerged. After a brief water rinse, the ants were soaked for 5 min in Kodak Microdal-X developer. The ants were then washed in 3% acetic acid and dehydrated in an alcohol series. The antennae were removed and embedded in Cytoseal for light microscopy. The results (FIG. 2) show that various types of porous sensilla occur on the female antenna, nearly all on the club. By contrast, the male antenna is uniformly covered with nearly identical porous *sensilla tricodea*. These anatomical observations suggest that the male fire ant is sensitive to a limited range of odor and pheromone signals compared to the female. Male fire ants do not care for brood, forage, or maintain and defend the nest. Their sole function in the colony is to participate in nuptial flights. This behavior pattern, combined with the simple sensilla pattern on the antenna, lead to the inference that male fire ants are sensitive to a limited number of pheromones and may have only a few pheromone-binding proteins.

Example 2

Isolation and Amino Acid Sequence Analysis of a Putative Pheromone-Binding Protein from Male Fire Ants This example demonstrates how a pheromone-binding protein sequence is obtained. Two hundred and fifty male fire ants were collected as described in Example 1. The antennae were removed by dissection on a −20° C. cold plate under a dissecting microscope and stored at −20° C. The antennae were transferred to a small ceramic mortar and, under a dissecting microscope, ground with a pestle in 40 μL of "rehydration buffer" prepared from a mixture of 12 g urea, 125 μL pH 3-10 IPG buffer (Pharmacia), and 16 mL deionized water. The resulting suspension of antenna fragments in buffer was transferred to a 1.5 mL plastic centrifuge tube and the mortar was rinsed with 20 μL of rehydration buffer, which was combined with the antenna fragment suspension in the centrifuge tube. The tube was centrifuged at 4000×g. The supernatant was diluted with 230 μL of rehydration buffer and placed in an Immobiline Dry Strip Reswelling Tray (Pharmacia) along with a 13 cm pH 3-10 Immobiline Dry Strip (Pharmacia).

After rehydration, the strip was subjected to isoelectric focusing at 3500 V for 5 hrs. The strip was then cut to produce a pH 3-6.5 half ("acidic") and a pH 6.5-10 half ("basic"). The half strips were separately equilbrated for 10 min in 0.5 M Tris buffer, pH 6.8 containing 0.25% dithiothreitol and 10 min in a solution prepared from 2 mL of 0.5 M Tris buffer, pH 6.8, 7.2 g urea, 6 mL glycerol, 0.2 g sodium dodecyl sulfate, 6.7 mL deionized water, and 90 mg iodoacetamide. The strips were then individually applied to the tops of 12% 8.5×6×0.75 cm polyacrylamide gels prepared according to the method of Laemmli (1970) and containing 1 cm stacking gels. Electrophoresis was performed for 45 min at 200 V. The gels were then soaked for 5 min in 3 mM CAPS buffer, pH 11 containing 10% methanol and electroblotted to PVDF film by the method of Matsudaira (1987) (e.g. 1 hr at 100 V in a BioRad Mini Trans-Blot Electrophoretic Transfer Cell). The PVDF films were stained for 1 min with 0.1% Coomassie R250 in 50% methanol and destained for approximately 5 min with a solution of 50% methanol, 10% acetic acid.

Two dimensional gel electrophoresis of extracts from whole male fire ant antennae shows one major spot at low apparent molecular weight and acidic isoelectric point (FIG. 1). This protein is near the range observed for OBP/PBPs in other insects. Further analysis of this protein by automated Edman degradation shows that the N-terminal sequence is TEGEQSGTQPQLS (SEQ ID NO:3). The sequence was used to design degenerate PCR primers. A 700 nucleotide RT-PCR product was obtained using these primers with male fire ant antennal RNA. This product was inserted into a pGEM vector and cloned in *E. coli*. The full DNA sequence of the insert was determined (SEQ ID NO:1). The derived protein sequence contained the expected N-terminal protein sequence (SEQ ID NO:2). A BLAST search indicated the protein as being 23% identical to apolipophorin-III (ALP-III) from *Derobrachus geminatus* (Smith et al., 1994) and 50% identical to an uncharacterized protein from the *Apis mellifera* brain EST library (gi:15354591).

ALP-III is known to function as a lipid-binding protein (Narayanaswami and Ryan, 2000). A member of the ALP-III family was found to be expressed in a pheromone-secreting gland of *Epiphyas postvittana* (Liu et al., 2002). Thus, ALP-III-like proteins can have a pheromone-related function. ALP-III-like proteins should be included in a list of insect antennal pheromone-binding proteins. The actual role of ALP-III in pheromone physiology may be binding of metabolic precursors and break-down products of pheromones, pheromone transport to or removal from the hemolymph, or pheromone binding in the olfactory reception process.

Example 3

Isolation and Amino Acid Sequence Analysis of a Putative Pheromone-Binding Protein from Male Fire Ants Identified as W3

As described in Example 2 above, two hundred and fifty male fire ants were collected. The antennae were removed by dissection on a −20° C. cold plate under a dissecting microscope and stored at −20° C. The antennae were transferred to a small ceramic mortar and, under a dissecting microscope, ground with a pestle in 40 μL of "rehydration buffer" prepared from a mixture of 12 g urea, 125 μL pH 3-10 IPG buffer (Pharmacia), and 16 mL deionized water. The resulting suspension of antenna fragments in buffer was transferred to a 1.5 mL plastic centrifuge tube and the mortar was rinsed with 20 μL of rehydration buffer, which was combined with the antenna fragment suspension in the centrifuge tube. The tube was centrifuged at 4000×g. The supernatant was diluted with 230 μL of rehydration buffer and placed in an Immobiline Dry Strip Reswelling Tray (Pharmacia) along with a 13 cm pH 3-10 Immobiline Dry Strip (Pharmacia).

After rehydration, the strip was subjected to isoelectric focusing at 3500 V for 5 hrs. The strip was then cut to produce a pH 3-6.5 half ("acidic") and a pH 6.5-10 half ("basic"). The half strips were separately equilbrated for 10 min in 0.5 M Tris buffer, pH 6.8 containing 0.25% dithiothreitol and 10 min in a solution prepared from 2 mL of 0.5 M Tris buffer, pH 6.8, 7.2 g urea, 6 mL glycerol, 0.2 g sodium dodecyl sulfate, 6.7 mL deionized water, and 90 mg iodoacetamide. The strips were then individually applied to the tops of 12% 8.5×6×0.75 cm polyacrylamide gels prepared according to the method of Laemmli (1970) and containing 1 cm stacking gels.

Electrophoresis was performed for 45 min at 200 V. The gels were then soaked for 5 min in 3 mM CAPS buffer, pH 11 containing 10% methanol and electroblotted to PVDF film by the method of Matsudaira (1987) (e.g. 1 hr at 100 V in a BioRad Mini Trans-Blot Electrophoretic Transfer Cell). The PVDF films were stained for 1 min with 0.1% Coomassie R250 in 50% methanol and destained for approximately 5 min with a solution of 50% methanol, 10% acetic acid.

The major protein spot was identified at relative molecular weight 14,000 and pI 3.5, called W3. N-terminal sequence analysis of W3 was performed in a Procise cLC492 gas phase sequencer. The sequence obtained was:

W3 GDLGLYPDEL (SEQ ID NO:4)

This sequence does not correspond to any known protein in the NCBI database, using a BLAST search. However, the sequence LY-D is similar to a sequence near the amino terminus of the CSP identified in the antenna of the Argentine ant (Ishida et al., 2002).

The W3 sequence may be used, as described in Example 2 above, to prepare PCR primers to obtain the full DNA and protein sequences from antennal cDNA.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altner and Prillinger, *Int. Rev. Cytol.,* 67:69-139, 1980.
Beuckmann et al., *Biochemistry,* 38:8006-8013, 1999.
Breer et al., *Nature,* 344:65-68, 1990.
Briand et al., *FEBS Lett.,* 476:179-185, 2000.
Caron et al., *J. Biol. Chem.,* 251:2374-2384, 1976.
Catimel et al., *J. Chrom.,* A869:261-273, 2000.
Danty et al, *J. Neuroscience,* 19:7468-7475, 1999.
Davis and Han, *Curr. Biol.,* 6:146-148, 1996.
Du and Prestwick, *Biochemistry,* 34:8726-8732, 1995.
Flower, *Biochem. J.,* 318:1-14, 1996.
Gronenberg et al., *J. Exp. Biol.,* 199:2011-2019, 1996.
Grotewiel et al., *Nature,* 391:455-460, 1998.
Hansson and Anton, *Annu. Rev. Entomol.,* 45:203-231, 2000.
Hekmat-Scafe et al., *J. Neuroscience,* 17:1616-1624, 1997.
Hildebrand and Shepard, *Annu. Rev. Neurosci.,* 20:595-631, 1997.
Holden et al., *EMBO J.,* 6:1565-1570, 1987.
Hölldobler and Wilson, In: *The Ants,* Belknap Press, Cambridge, Mass., 1990.
Horst et al., *Proc. Natl. Acad. Sci. USA,* 98:14374-14379, 2001.
Ishida et al., *Naturwiss,* 89:505-507, 2002
Jouvenaz et al., *Florida Ent.,* 60:275-279, 1977.
Keller and Ross, *Nature,* 394:573-575, 1998.
Kim et al., *Genetics,* 150:711-721, 1998.
Korchi et al., *FEBS Lett.,* 449:125-128, 1999.
Krieger and Breer, *Science,* 286:720-723, 1999.
Krieger et al., *Insect Biochem. Molec. Biol.,* 29:255-267, 1999.
Krieger and Ross, *Science,* 295(5553):328-332, 2002.
Laemmli, *Nature,* 227:680-685, 1970.
Laurent and Davidowitz, *Science,* 265:1872-1875, 1994.
Leal et al., *FEBS Lett.,* 464:85-90, 1999.
Liu et al., *Proc. Natl. Acad. Sci. USA,* 99(2):620-624, 2002.
Mameli et al., *Insect Biochem. Molec. Biol.,* 26:875-882, 1996.
McLeod et al., *Nature,* 395:693-698, 1998.
Matsudaira, *J. Biol. Chem.,* 262:10035-10038, 1987.
Mori et al., *Insectes Sociaux,* 47:7-10, 2000.
Narayanaswami and Ryan, Biochim. Biophys. Acta, 1483:5-36, 2000.
Navasero and Elzen, *Proc. Ent. Soc. Wash.,* 93:737-747, 1991.
Paesen, and Happ, *Insect Biochem. Molec. Biol.,* 25:401-408, 1995.
Pelosi and Maida, *Comp. Biochem. Physiol.,* 111B:503-514, 1995.
Picimbon and Leal, *Insect Biochem. Molec. Biol.,* 29:973-978, 1999.
Pikielny et al., *Neuron.,* 12:35-49, 1994.
Pilpel and Lancet, *Nature,* 398:285-286, 1999.
Ross and Keller, *Proc. Natl. Acad. Sci. USA,* 95:14232-14237, 1998.
Rothemund et al., *Structure,* 7:1325-1332, 1999.
Rubin et al., *Science,* 287:2204-2215, 2000.
Sandler et al., *Chemistry and Biology,* 7:143-151, 2000.
Shevchenko et al., *Analytical Chemistry,* 68:850-858, 1996.
Skoulakis et al., *Neuron.,* 11:197-208, 1993.
Smith et al., *J. Lipid Res.,* 35:1976-1984, 1994.
Steinbrecht and Stankiewicz, *J. Insect Physiol.,* 45:785-790, 1999.
Tsuchihara et al., *FEBS Lett.,* 478:299-303, 2000.
Vincent et al., *J. Mol. Biol.,* 300:127-139, 2000.
Vogt et al., *J. Neurobiology,* 22:74-84, 1991.
Willett and Harrison, *Insect Biochem. and Mol. Biol.,* 29:277-284, 1999.
Wojtasek et al., *Biochem. Biophys. Res. Commun.,* 250:217-222, 1998.
Wojtasek and Leal, *J. Biol. Chem.,* 274:30950-30956, 1999.
Zacharuk, *Comprehen. Insect Physiol., Biochem. and Pharm.,* 6:1-69, 1985.

What is claimed is:

1. A method of identifying an insect pheromone comprising:
   a) obtaining one or more insect pheromone-binding proteins;
   b) placing the one or more pheromone-binding proteins on a solid support;
   c) obtaining a composition comprising an extract of whole insects, parts of insects, larvae, pupae, or nest middens, wherein the composition potentially comprises one or more insect pheromones;
   d) contacting the one or more pheromone-binding proteins on the solid support with the composition under conditions conducive to allow at least one suitable pheromone, if present, to bind to at least one of the pheromone binding proteins on the solid support; and
   e) eluting any molecule specifically bound to the one or more pheromone-binding proteins on the solid support, wherein any eluted molecule is identified as a pheromone.

2. The method of claim 1, wherein at least one of the one or more pheromone-binding proteins is a recombinant pheromone-binding protein.

3. The method of claim 2, wherein the recombinant pheromone-binding protein is obtained by a method comprising amplifying a nucleic acid sequence encoding a polypeptide comprising the pheromone-binding protein.

4. The method of claim 3, wherein the nucleic acid sequence of the pheromone-binding protein is amplified by a method comprising:
   a) using PCR primers to amplify a nucleic acid sequence from a DNA library of the insect sample, said PCR primers constructed using partial or complete sequence analysis of the pheromone binding protein; and
   b) expressing the nucleic acid sequence in an expression system to produce the pheromone-binding protein.

5. The method of claim 4, wherein the DNA library comprises the S. invicta genome.

6. The method of claim 1, wherein the solid support comprises agarose, plastic, or glass.

7. The method of claim 1, wherein the pheromone-binding protein is covalently attached to the solid support.

8. The method of claim 1, wherein the extract of whole insects, parts of insects, larvae, pupae, or nest middens is further defined as a solvent extract.

9. The method of claim 8, wherein the solvent comprises pentane, hexane, methylene chloride, chloroform, methanol, or diethyl ether, or a combination thereof.

10. The method of claim 1, wherein the composition is further defined as a vapor.

11. The method of claim 1, further comprising isolating or purifying any eluted molecule.

12. The method of claim 11, further comprising using the isolated or purified eluted molecule to attract an insect to poison, to repel an insect from an area intended to be kept pest-free, or to interfere with insect behavior, such as mating or foraging, resulting in the extermination of the insect.

13. The method of claim 1, further comprising performing a partial or complete sequence analysis of the one or more pheromone-binding proteins prior to placing the one or more pheromone-binding proteins on a solid support.

14. The method of claim 1, wherein more than one insect pheromone binding protein is obtained in step a).

15. The method of claim 14, further comprising separating the pheromone binding proteins.

16. The method of claim 15, wherein the pheromone binding proteins are separated by electrophoresis or isoelectric focusing followed by SDS-PAGE.

17. The method of claim 1, wherein the one or more insect pheromone-binding proteins is obtained from a member of the genus *Anopheles*, an aphid, a member of the genus *Solenopsis*, or a scale insect.

18. The method of claim 1, wherein the one or more insect pheromone-binding proteins is from red imported fire ants.

19. The method of claim 1, further comprising diluting the eluted pheromone.

20. The method of claim 18, wherein the red imported fire ants are male ants, worker ants, monogyne queen ants, or polygyne queen ants.

21. The method of claim 1, wherein the composition comprises an extract of larvae.

22. The method of claim 1, wherein the composition comprises an extract of pupae.

23. The method of claim 1, wherein the composition comprises an extract of nest middens.

24. The method of claim 1, wherein obtaining one or more insect pheromone-binding proteins further comprises:
   a) obtaining a first sequence analysis of at least one pheromone-binding protein; and
   b) selecting one or more pheromone-binding protein of interest from the sequenced pheromone-binding proteins.

25. The method of claim 24, wherein the first sequence analysis is performed by mass spectrometry or Edman degradation.

26. The method of claim 24, wherein the sequence analysis is a partial sequence analysis.

27. The method of claim 24, wherein selecting the pheromone-binding protein of interest comprises:
   a) comparing the first sequence analysis with a second sequence of a known insect pheromone-binding protein; and
   b) choosing one or more of the sequenced pheromone-binding proteins that have a sequence similar to the second sequence of the known insect pheromone-binding protein.

28. The method of claim 1, wherein obtaining one or more insect pheromone-binding proteins further comprises performing a sequence analysis of at least one of the pheromone-binding proteins, determining a nucleic acid sequence that encodes the sequenced pheromone-binding protein, and recombinantly expressing the sequenced pheromone-binding protein from the nucleic acid sequence that encodes the pheromone-binding protein.

29. The method of claim 28, wherein the sequence analysis is a partial sequence analysis.

30. The method of claim 28, wherein recombinantly expressing the one or more pheromone-binding protein from the nucleic acid sequence further comprises using the pheromone-binding protein sequence to construct a primer, and using the primer to identify a genomic sequence from an existing DNA library.

* * * * *

UNITED STATES PATENT AND TRADEMARK OFFICE
CERTIFICATE OF CORRECTION

PATENT NO. : 7,741,037 B2
APPLICATION NO. : 11/355444
DATED : June 22, 2010
INVENTOR(S) : Robert David Renthal It is certified that error appears in the above-identified patent and that said Letters Patent is hereby corrected as shown below:

In title page, item (56) References Cited - FOREIGN PATENT DOCUMENTS, insert
--EP   1230856        8/2002
  WO  WO 96/19919    7/1996--.

Signed and Sealed this

Fifth Day of October, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 685
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1

```
gagcaaagtg ggactcagcc gcaactgtcg gattacatcc gggacgccca aactgccatc      60
agcagcttgg gcactcagat tcaggagcat ctcaacttgc ctaaccaaga ggaacttgcc     120
aataccttca aggagcagag caccaatttc gccaacaatg ttcaggcgta cctgcaaaac     180
ataaccgacg aggtcaaggc caagagtcct gaattggaag atttctggac aaatatgaag     240
accaaactgt ccgaagctgt cgacaattta catatcaatc ccgaaacgac ggagcaagtg     300
aatcagctcg cgccaagttt caagagggcg tacagactct cgtaacgaa tcggagaacg      360 ccgccaagac catcagtgag aattccggca aggttcaaga gagtatcgcc aagattacca     420
agcaggcgat cgacatcgct gtgaaagctt cgcaaaactt gaaccaacag ttgcagcagg     480
ctacgacgcc gcaaccataa cggttgacaa attattctcg tgtaaattag tataccgcga     540
acgattgtct tggacgattg aaatttttcgt ccgcaagagg aggaggattt ttctccacat     600
tcaccaagtc aatctatgta attttacacc atgtcgtaaa catacttgaa taaaagtact     660
cgattcttaa aaaaaaaaaa aaaaa                                            685
```

<210> SEQ ID NO 2
<211> LENGTH: 169
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 2

Thr Glu Gly Glu Gln Ser Gly Thr Gln Pro Gln Leu Ser Asp Tyr Ile
 1               5                  10                  15

Arg Asp Ala Gln Thr Ala Ile Ser Ser Leu Gly Thr Gln Ile Gln Glu
            20                  25                  30

His Leu Asn Leu Pro Asn Gln Glu Glu Leu Ala Asn Thr Phe Lys Glu
        35                  40                  45

Gln Ser Thr Asn Phe Ala Asn Asn Val Gln Ala Tyr Leu Gln Asn Ile
    50                  55                  60

Thr Asp Glu Val Lys Ala Lys Ser Pro Glu Leu Glu Asp Phe Trp Thr
65                  70                  75                  80

Asn Met Lys Thr Lys Leu Ser Glu Ala Val Asp Asn Leu His Ile Asn
                85                  90                  95

Pro Glu Thr Thr Glu Gln Val Asn Gln Leu Arg Ala Lys Phe Gln Glu
           100                 105                 110

Gly Val Gln Thr Leu Val Thr Glu Ser Glu Asn Ala Ala Lys Thr Ile
       115                 120                 125

Ser Glu Asn Ser Gly Lys Val Gln Glu Ser Ile Ala Lys Ile Thr Lys
   130                 135                 140

Gln Ala Ile Asp Ile Ala Val Lys Ala Ser Gln Asn Leu Asn Gln Gln
145                 150                 155                 160

```
Leu Gln Gln Ala Thr Thr Pro Gln Pro
            165

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Gly Asp Leu Gly Leu Tyr Pro Asp Glu Leu
  1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Thr Glu Gly Glu Gln Ser Gly Thr Gln Pro Gln Leu Ser
  1               5                  10
```